US006877352B1

(12) United States Patent
Schlereth

(10) Patent No.: US 6,877,352 B1
(45) Date of Patent: Apr. 12, 2005

(54) SYSTEM FOR SECURING A SUTURE TO A NEEDLE IN A SWAGED FASHION

(76) Inventor: David Schlereth, 8657 Villa La Jolla Dr., Ste. 223, La Jolla, CA (US) 92037

(*) Notice: Subject to any disclaimer, the term of this patent is extended or adjusted under 35 U.S.C. 154(b) by 0 days.

(21) Appl. No.: 10/617,416

(22) Filed: Jul. 10, 2003

(51) Int. Cl.[7] ............................................. B21D 39/00
(52) U.S. Cl. ...................... 72/409.19; 72/416; 29/282; 29/283.5; 606/226
(58) Field of Search .................. 72/409.19, 409.01, 72/416; 29/283.5, 237, 282; 606/226

(56) References Cited

U.S. PATENT DOCUMENTS

| | | | |
|---|---|---|---|
| 4,538,443 A | * | 9/1985 | Gooding ........................ 72/416 |
| 4,799,311 A | * | 1/1989 | Matsutani ...................... 29/709 |
| 5,234,438 A | | 8/1993 | Semrad ........................ 606/108 |
| 5,350,373 A | * | 9/1994 | Colligan ......................... 606/1 |
| 5,448,823 A | * | 9/1995 | Granger et al. ................. 29/721 |
| 5,485,668 A | * | 1/1996 | Demarest et al. .............. 29/517 |
| 5,755,729 A | | 5/1998 | de la Torre et al. .......... 606/148 |
| 5,903,966 A | * | 5/1999 | Sonderegger ................... 29/464 |
| 5,908,426 A | | 6/1999 | Pierce .......................... 606/139 |
| 5,919,199 A | | 7/1999 | Mers Kelly et al. .......... 606/139 |
| 5,943,765 A | * | 8/1999 | Shikakubo et al. ............ 29/705 |
| 6,604,403 B1 | * | 8/2003 | Eslambolchi et al. .......... 72/416 |

* cited by examiner

Primary Examiner—Daniel C. Crane
(74) Attorney, Agent, or Firm—Goldstein Law Offices, P.C.

(57) ABSTRACT

A crimper having a crimping block and a crimping lever. The crimping block has a top surface, a first end, and an opposite second end. The first end provides receptacles which each allow a swaged needle having a needle hole end having a needle hole to be inserted therein. The second end has suture channels which allow a suture to be inserted into the crimping block such that the suture is guided toward the needle end hole. The top surface has a plurality of crimping openings which each expose one of the receptacles and the needle hole end therein. The crimping lever has a plurality of protrusions which are aligned with the crimping openings such that one of the projections engages the needle end and mechanically crimp the needle end to secure the suture therein. The needle may then be withdrawn from the receptacle with the suture secured therein.

9 Claims, 2 Drawing Sheets

SYSTEM FOR SECURING A SUTURE TO A NEEDLE IN A SWAGED FASHION

BACKGROUND OF THE INVENTION

The present invention relates to a system for securing a suture to a needle in a swaged fashion and more particularly pertains to allowing a suture to be easily secured and crimped within an open end of a suture needle so that the suture extends longitudinally from the needle.

Sutures are typically attached to a needle in either swaged or eyed fashions. Eyed needles must be threaded, a time-consuming procedure for a scrub person. This presents the disadvantage of having to pull a double strand of suture material through tissue, creating a larger hole, presenting additional resistance, and resulting in additional tissue disruption and trauma. It is a primary consideration when selecting a surgical needle that the tissue being sutured should be altered as little as possible by the needle since the only purpose of the needle is to introduce the suture into the tissue. Certain delicate tissue, such as eye tissue, is extremely subject to trauma, making the double strand highly undesirable. A further danger is presented in 'eyed' sutures, in that the suture may become unthreaded while the surgeon is using it.

Swaged needles seek to employ a nearly continuous, longitudinal connection between the suture and needle, such that the suture is, for all intents and purposes, a trailing continuation of the needle. This configuration joins the needle and suture together as a continuous unit—one that is convenient to use and minimizes trauma. In this arrangement, the suture is placed into a hole drilled into the needle end. The suture is usually secured within these holes. One problem with this arrangement is knowing whether the suture has been sufficiently secured within the hole, so that it does not "break free" during suturing.

Currently, swaged needles are available pre-packaged with sutures already joined thereto. Both needles and sutures, however, are available in several different sizes and types. In commercially available pre-sutured swaged needles, each needle is already matched with a suture. This arrangement often requires the surgeon to either compromise on the ideal needle or suture he/she would prefer to use. Ideally, the surgeon should be the one to match the suture to the needle for the given application. On the other hand, producing every combination of suture and needle in a pre-paired fashion is not commercially viable from a manufacturing standpoint, and would require medical institutions to stock an unreasonably large variety of needle-suture pairs.

Further, pre-swaged needles are disproportionally expensive compared to the cost of swaged needles and bulk sutures available on a spool. Accordingly, it would be highly desirable to provide a system which allows the surgeon to select a swaged needle and easily mate a suitable length of the desired suture thereto.

The present invention attempts to solve the above-mentioned problem by providing a crimping block which allows a swaged end suture needle to be mated with any chosen suture.

The use of surgical devices is known in the prior art. More specifically, surgical devices heretofore devised and utilized for the purpose of facilitating surgical procedures are known to consist basically of familiar, expected and obvious structural configurations, notwithstanding the myriad of designs encompassed by the crowded prior art which have been developed for the fulfillment of countless objectives and requirements.

By way of example, U.S. Pat. No. 5,908,429 to Pierce discloses a suture needle capable of applying a suture by retracting the sheath and applying tension. U.S. Pat. No. 5,234,438 to Semrad discloses means for feeding a suture through a needle for use in a tunneling procedure. U.S. Pat. No. 5,755,729 to de la Torres discloses a device for loading a needle with a length of suture. U.S. Pat. No. 5,919,199 to Mers Kelly discloses an additional suture device.

While these devices fulfill their respective, particular objective and requirements, they are not as suitable for the purposes of the present invention as described hereinafter.

SUMMARY OF THE INVENTION

In the view of the foregoing disadvantages inherent in the known types of surgical devices now present in the prior art, the present invention provides system for securing a suture within in a swaged fashion. As such, the general purpose of the present invention, which will be described subsequently in greater detail, is to provide a new and improved system for crimping a suture in a swaged needle end which has all the advantages of the prior art and none of the disadvantages.

It is another object of the invention to allow the suture and needle to be mated with only minimal manual dexterity. A crimping block is provided which allows the needle to be placed in a first side thereof, and allows a suture to be inserted into an opposite side thereof, whereby the suture is guided toward the needle end hole. A crimping lever is lowered onto the crimping block to engage the needle and mechanically secure the suture within the needle end hole.

It is another object of the invention to accommodate needles of various sizes. Accordingly, multiple needle receptacles are provided on the first end of the crimping block. The user can choose a suitable one of the needle receptacles to use for the crimping operation.

It is a further object of the invention to maintain sterility of both the needle and suture. Accordingly, by minimizing dexterity required for the crimping operation, the actual handling of the needle and suture is minimized.

To attain this, the present invention essentially comprises a crimper having a crimping block and a crimping lever. The crimping block has a top surface, a first end, and an opposite second end. The first end provides receptacles which each allow a swaged needle having a needle hole end having a needle hole to be inserted therein. The second end has suture channels which allow a suture to be inserted into the crimping block such that the suture is guided toward the needle end hole. The top surface has a plurality of crimping openings which each expose one of the receptacles and the needle hole end therein. The crimping lever has a plurality of protrusions which are aligned with the crimping openings such that one of the projections engages the needle end and mechanically crimps the needle end to secure the suture therein. The needle may then be withdrawn from the receptacle with the suture secured therein.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved suture means for securing any desired suture to a swaged needle, which has all the advantages of the prior art surgical devices and none of the disadvantages.

It is another object of the present invention to provide a new and improved suture means for securing any desired suture to a swaged needle, which may be easily and efficiently manufactured and marketed.

It is a further object of the present invention to provide a new and improved suture means for securing any desired suture to a swaged needle which is of durable and reliable construction.

An even further object of the present invention is to provide a new and improved suture means for securing any desired suture to a swaged needle which is susceptible of a low cost of manufacture with regard to both materials and labor, and which accordingly is then susceptible of low prices of sale to the consuming public, thereby making the use of a multitude of swaged suture-needle pairings economically feasible.

These together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

Similar reference numerals refer to similar components through the various figures.

DESCRIPTION OF THE PREFERRED EMBODIMENT

Figure 1:
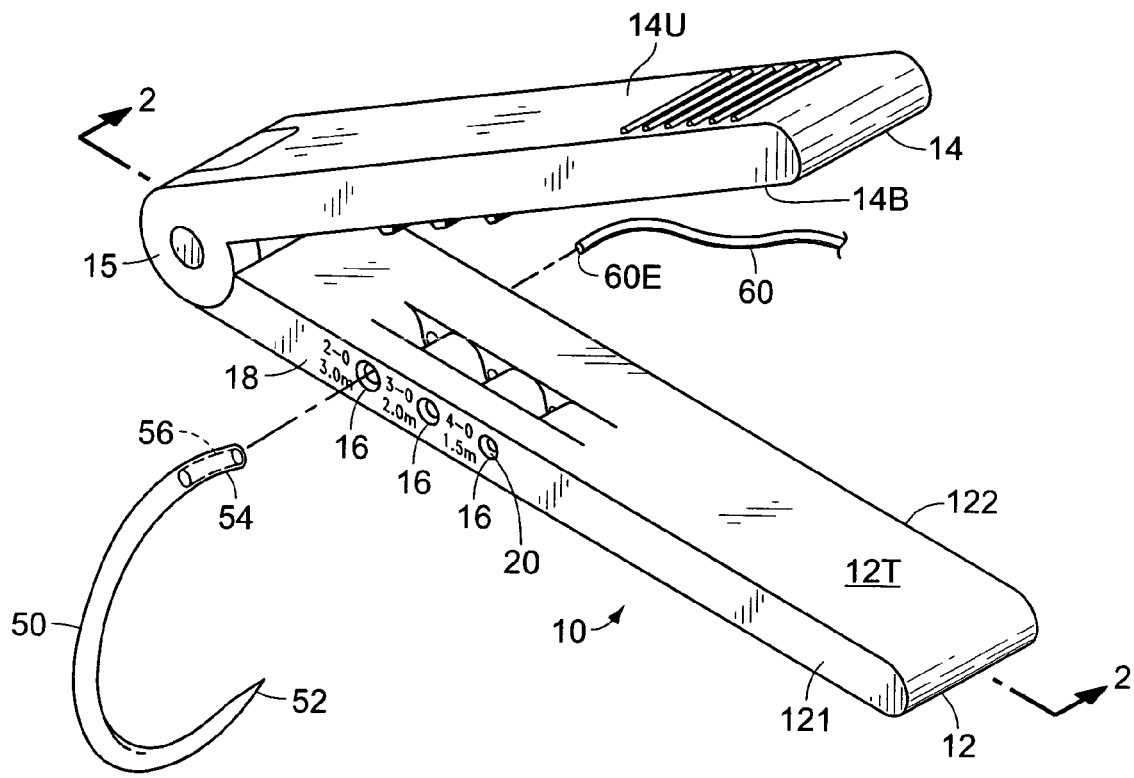
FIG. 1 is a perspective view of the preferred embodiment of the invention wherein a crimping block and crimping lever for securing a suture in a swaged needle end is illustrated in accordance with the principles of the present invention.

With reference now to the drawings, and in particular, to FIGS. 1 through 5 thereof, the preferred embodiment of the system for mating a desired suture to a desired needle in a swaged fashion embodying the principles and concepts of the present invention is illustrated. In accordance with the principles of the present invention, a crimper, generally designated by the reference number 10 will be described.

Specifically, it will be noted in the various figures that the invention relates to a system for allowing a surgeon to choose a desired suture and a desired needle and for securing that suture within swaged needle end. In its broadest context, the system employs a swaged needle 50, a suture 60, and the crimper 10. Such components are individually configured and correlated with respect to each other so as to attain the desired objective.

The suture 60 has a free end 60E which is also referred to as a suture end 60E herein. The swaged needle 50 has a generally arcuate configuration. The swaged needle 50 has a pointed end 52 and a blunt needle hole end 54. The needle hole end 54 has a needle hole 56 extending longitudinally inward. The needle hole 56 is dimensioned for longitudinally receiving the free end 60E of the suture 60 therein. The needle hole end 54 is configured so that when squeezed, the walls will collapse, indent, flatten, etc., around the suture 60 to narrow the needle hole 56 and thereby mechanically secure the suture 60 therein.

The crimper 10 has a crimping block 12 having a top 12T, a first side 121, and an opposite second side 122. The first side 121 and second side 122 are substantially orthogonal to the top 12T. A crimping lever 14 has a bottom surface 14B and an upper surface 14U. The crimping lever 14 is hingeably attached to the crimping block 12 with a hinge joint 15, such that the crimping lever 14 is capable of pivotally extending in a crimping position wherein it is substantially parallel to the crimping block 12 with the bottom surface 14B of the crimping lever 14 substantially coincident with the top surface 12T of the crimping block 12; and extending in an open position, wherein the crimping lever 14 forms an acute angle with the crimping block 14. In this regard, the hinge joint 15 may be configured so that the crimping lever 14 is biased toward the open position, and the user must exert some minimal effort upon the crimping lever 14 to bring it to the crimping position.

Still referring to FIG. 1, the crimping block 12 has a plurality of needle receptacles 16 extending therein from the first side 121 for allowing the insertion of the hole end 54 of the needle 50. The needle receptacles 16 are of varying diameter for accepting different size needles 50, and may be labeled by needle size indicia 18 which indicates the size of needles suitable and most appropriate for each of said receptacles 16, using any desired measurement convention. A receptacle surface bevel 20 is preferably provided at the first side 121 concentric with each receptacle 16. Each receptacle surface bevel 20 is an enlargement of the receptacle 16 thereat, to easily guide the needle 50 into said receptacle 16— even if not precisely aligned by the user.

Figure 3:
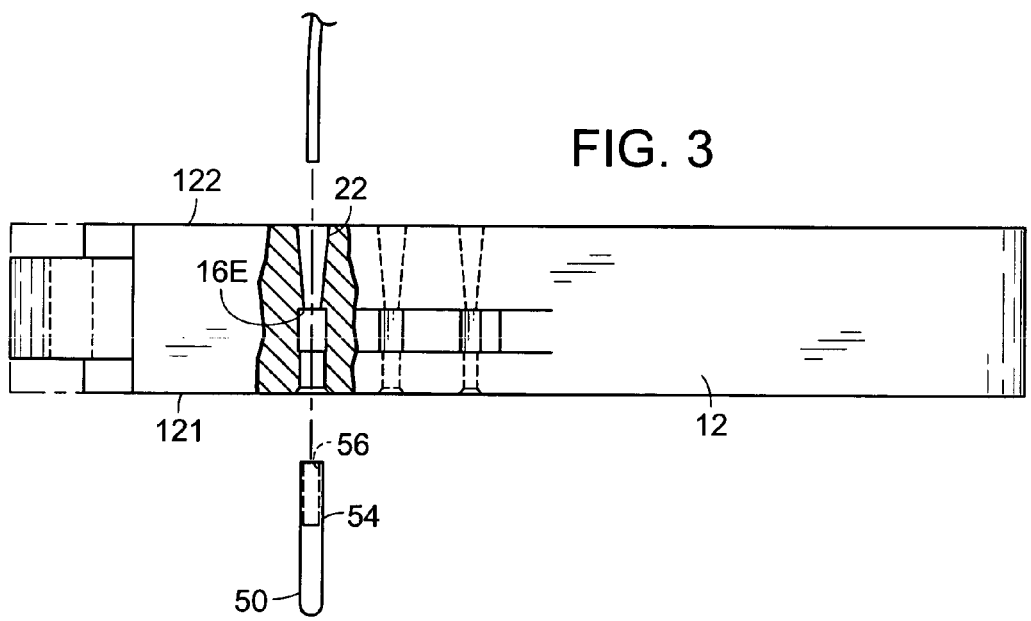
FIG. 3 is a top plan view of the crimping block, with the crimping lever removed, illustrating a first step in securing a chosen suture and needle, where the needle is introduced into one of the receptacles at a first side of the crimping block, and a suture is introduced into one of the suture channels at a second side of the crimping block.

Referring now to FIG. 3, each receptacle 16 has an internal end wall 16E, substantially midway between the first side 121 and second side 122 to limit the travel of the needle 50 into the crimping block 12. Associated with each receptacle 16 is a suture channel 22 extending into the second side, substantially coaxially with that receptacle 16, and in communication with the receptacle 16 through the end wall 16E thereof. Each suture channel 22 is preferably flared toward the second end 122, and consequently tapered inward toward the end wall 16E, so as to guide the suture end 60E inserted into the suture channel 22 toward the end wall 16E, thus toward the needle hole end 54 resting thereagainst, and ultimately into the needle hole 56.

Figure 4:
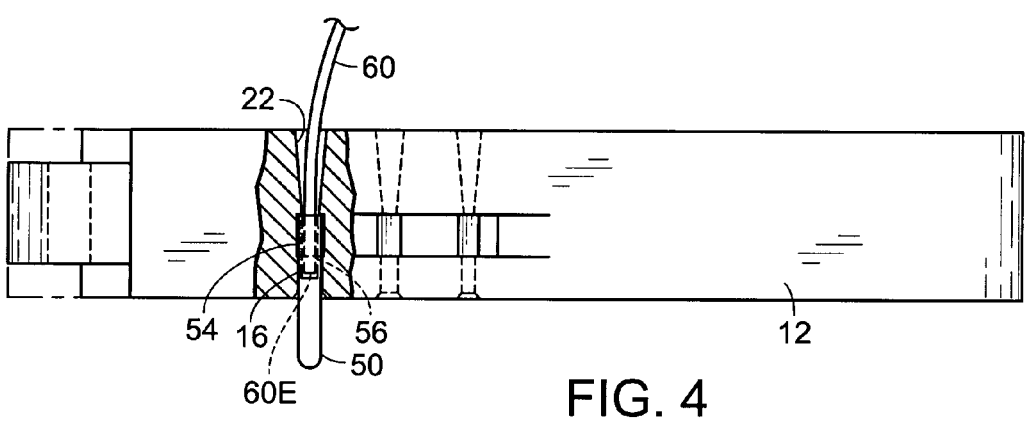
FIG. 4 is a top plan view, similar to FIG. 3, except wherein the suture has been guided into the needle end hole by one of the suture channels.

In particular, in FIG. 4, the needle 50 has been fully inserted into one of the receptacles 16 of the crimping block 12, which is sized to closely accommodate that needle 50. The needle hole end 54 needle 50 has come to rest against the end wall 16E with the needle hole 56 exposed thereat. In addition, the suture end 60E has been inserted into the suture channel 22 associated with that receptacle 16, and has been guided by the tapered/flared nature of the suture channel 22 toward and past the end wall 16E and fully into the needle hole 56.

Figure 2:
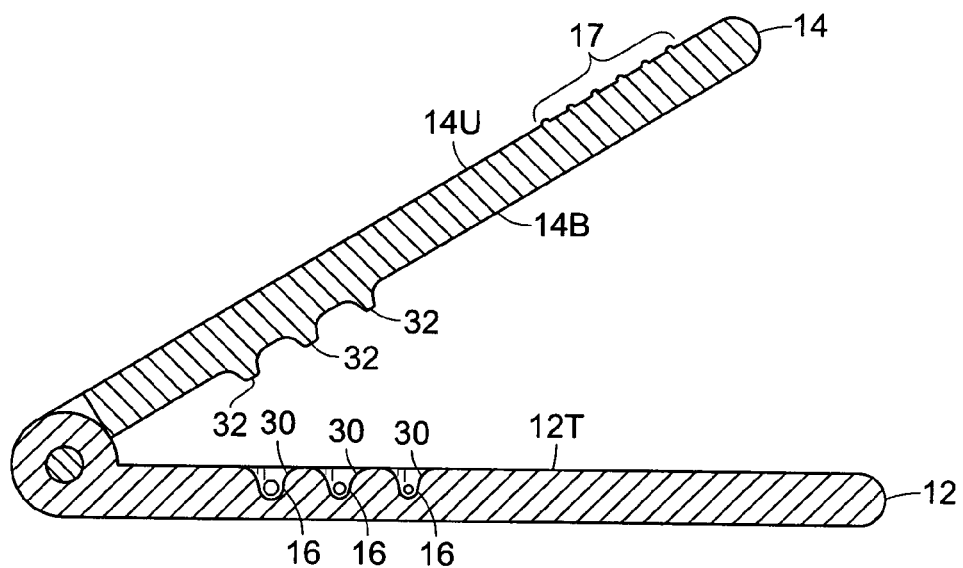
FIG. 2 is a cross sectional view of the crimping block and crimping lever of the present invention, illustrating the crimping openings in the crimping block, suture channels in communication therewith, and crimping projections in the crimping lever which are aligned to extend into the crimping openings when the crimping lever is pivoted downward.

Now, referring to FIG. 2, a plurality of crimping openings 30 are provided in the top surface 12T of the crimping block 12. The crimping openings 30 are in communication with the receptacles 16, such that when the needle 50 is fully inserted therein, the needle hole end 54 is exposed through the crimping openings. Also seen in FIG. 2, the bottom surface 14B of the crimping lever 14 has a plurality of protrusions 32 which are each shaped and aligned to extend into one of the crimping openings 30 when the crimping arm 14 is in the crimping position to engage and exert a concentrated force upon a needle 50 when located within said receptacle 16. The upper surface 14U of the crimping lever 14 has a ridged gripping surface 17 which facilitates the user in precisely applying force upon the crimping lever 14 to effect crimping of the needle 50.

Accordingly, when the needle 50 is fully inserted into the receptacle 16 and the suture is fully inserted into the needle hole 56 as illustrated in FIG. 4, the crimping arm is pivotally lowered by the user to the crimping position, and pressure is exerted upon the upper surface 14U of the crimping arm 14 by the user, such that the force exerted by the user is concentrated by one of the protrusions upon the needle hole end 54 by the protrusion 32 associated with that receptacle 16, to collapse the walls of the needle hole end 54 around the suture 60 and thereby create a mechanical connection between the suture 60 and needle 50. Generally to indicate that crimping has properly taken place, and audible "snap" will be produced as the walls of the needle hole end 54 'collapse'.

Figure 5:
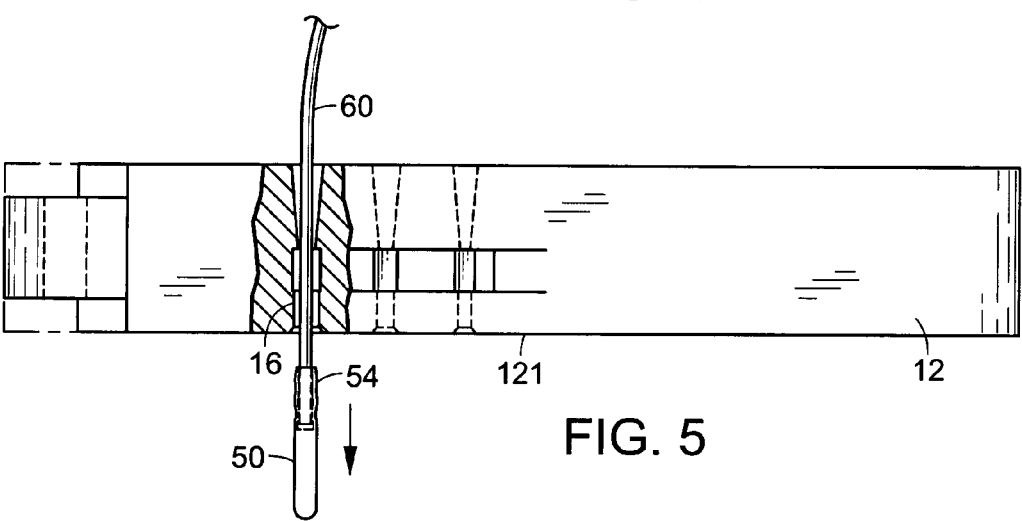
FIG. 5 is a top plan view, similar to FIG. 4, except wherein the needle has been crimped, the suture has been mechanically secured therein, and wherein the paired combination is being withdrawn from the crimping block.

Then, referring to FIG. 5, with the suture 60 and needle 50 mechanically connected such that the suture 60 extends longitudinally from the needle hole end 54, the needle 50 may be withdrawn from the receptacle 16 from the first end 121 of the crimping block 12, with the suture 60 following until the suture 60 is pulled fully from the first end 121 through the receptacle 16.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. A device for securing a suture to a swaged needle, the suture having a suture end, the swaged needle having a pointed end, and a blunt needle hole end having a needle hole extending longitudinally therein, comprising:

a crimping block having a top, a first end, a second end fully opposite from the first end, a receptacle extending into the crimping block from the first end, a suture channel associated and coaxial with said receptacle and extending into the crimping block from the second end, the suture channel in communication with the receptacle, and a crimping opening in communication with said receptacle; and a crimping arm, hingeably attached to the crimping block, having a bottom surface, having a crimping position wherein the bottom surface of the crimping arm selectively extends substantially parallel to the top surface of the crimping block, and having an open position wherein the crimping arm extends at an acute angle to the crimping block, the bottom surface having a protrusion associated with said receptacle such that when in the crimping position said protrusion extends into the crimping opening associated with said receptacle, such that when the needle hole end has been inserted into said receptacle and the suture has been inserted through the suture channel and into the needle hole, the protrusion may be pressed downward upon the needle to crimp the needle to mechanically connect the suture with the suture.

2. The device for securing a suture to a swaged needle as recited in claim 1, wherein the receptacle has an end wall substantially midway between the first and second sides of the crimping block for limiting travel of the needle hole end into the block; and wherein the suture channel is tapered inward toward the end wall for guiding the suture toward the end wall and into the needle hole of the needle in the needle hole end when the needle has been inserted into the receptacle.

3. The device for securing a suture to a swaged needle as recited in claim 2, wherein a plurality of receptacles are provided, the receptacles of varying diameters for accommodating various sized needles.

4. The device for securing a suture to a swaged needle as recited in claim 3, wherein the first side has needle size indicia for indicating the size of needles appropriate for use in each of the receptacles.

5. The device for securing a suture to a swaged needle as recited in claim 4, wherein each receptacle has a surface bevel at the first side for guiding the needle into said receptacle.

6. A method of securing a suture to a swaged needle, the suture having a suture end, the swaged needle having a pointed end, and a blunt needle hole end having a needle hole extending longitudinally therein, using a crimper including a crimping block and a crimping arm hingeably attached to the crimping block, the crimping block having a top, a first end, a second end fully opposite from the first end, a receptacle extending into the crimping block from the first end, a suture channel associated with said receptacle and extending into the crimping block from the second end, the suture channel in communication with the receptacle, and a crimping opening in communication with said receptacle, the crimping arm having a bottom surface having a protrusion, comprising the steps of:

inserting the needle into the receptacle by extending the needle hole end into the first side of the crimping block;

inserting the suture end into the needle hole by inserting the suture end into the suture channel;

connecting the suture and needle mechanically by crimping the needle hole end around the suture end by engaging the protrusion with the needle hole end by pivoting the crimping arm to a crimping position wherein the bottom surface thereof is substantially parallel to the top surface of the crimping block and pressing upon the crimping arm by the user; and withdrawing the mechanically connected suture and needle by withdrawing the crimping block from the first end, and pulling the suture through the crimping block out from the first end.

7. The method of securing a suture to a swaged needle as recited in claim 6, wherein the receptacle has an end wall substantially midway between the first and second end of the crimping block, the suture channel is in communication with the receptacle through the end wall; and wherein the step of inserting the needle into the receptacle further comprises inserting the needle into the receptacle until it reaches the end wall.

8. The method of securing a suture to a swaged needle as recited in claim 7, wherein a plurality of receptacles are provided of varying diameters; wherein suture channels are provided such that each is uniquely associated with one of the receptacles; and wherein the step of inserting the needle further comprises choosing one of the receptacles which closely diametrically matches the needle.

9. The method of securing a suture to a swaged needle as recited in claim 8, wherein each suture channel is tapered inward toward the end wall; and wherein the step of inserting the suture end into the needle hole further comprises guiding the suture end toward and past the end wall by the tapered suture channel.

\* \* \* \* \*